United States Patent [19]

Iwasaki et al.

[11] Patent Number: 5,150,821

[45] Date of Patent: Sep. 29, 1992

[54] APPARATUS FOR SEPARATE INJECTION OF REAGENT

[75] Inventors: Shuji Iwasaki, Fujisawa; Toshi Kagayama, Yokohama; Kazuya Kamata, Ebina, all of Japan

[73] Assignee: Tosoh Corporation, Yamaguchi, Japan

[21] Appl. No.: 505,399

[22] Filed: Apr. 6, 1990

[30] Foreign Application Priority Data

Apr. 7, 1989 [JP] Japan .................................. 1-88692

[51] Int. Cl.⁵ .............................................. B67D 5/60
[52] U.S. Cl. ............................... 222/132; 222/144.5; 222/309
[58] Field of Search ............... 222/132, 135, 137, 144, 222/255, 266, 309, 330, 144.5; 422/64, 65

[56] References Cited

U.S. PATENT DOCUMENTS

| 3,084,871 | 4/1963 | Puglis | 222/144 |
| 3,718,234 | 2/1973 | Bagguley | 222/135 |
| 3,727,799 | 4/1973 | Nixon | 222/144 |
| 3,756,783 | 9/1973 | Williams | 422/66 |
| 4,103,722 | 8/1978 | Zollinger | 222/144 |
| 4,159,784 | 7/1979 | D'Autry | 222/309 |
| 4,681,741 | 7/1987 | Hanaway | 222/137 |
| 4,710,355 | 12/1987 | Ushikubo | 222/135 |
| 4,982,877 | 1/1991 | Burton | 222/255 |

FOREIGN PATENT DOCUMENTS 7327427  2/1975  France .
1-44858  2/1989  Japan .

Primary Examiner—Andres Kashnikow
Assistant Examiner—Philippe Derakshani
Attorney, Agent, or Firm—Sughrue, Mion, Zinn, Macpeak & Seas

[57] ABSTRACT

An apparatus for selectively injecting a reagent into a reaction chamber from a plurality of reagent reservoirs disposed in a circular configuration includes a separate dispenser mounted on each reagent reservoir. A vertically extending rod having a horizontally extending lever connected thereto is positioned concentrically within the circular array of reservoirs and drive motors are provided for rotating and reciprocating the rod and lever to selectively engage and operate the desired dispenser. Each dispenser is provided with its own distribution tube which directs the reagent in the reservoir directly into a selected reaction chamber, thereby preventing cross contamination of the reagents.

4 Claims, 3 Drawing Sheets

APPARATUS FOR SEPARATE INJECTION OF REAGENT

BACKGROUND OF THE INVENTION

1. Field of the Invention

The present invention relates to an apparatus for separate injection of reagents which is employed for performing operations of selecting an arbitrary one out of a plurality of reagents prepared beforehand and injecting it separately into a reacting vessel in an installation wherein analytic operations such as a biochemical analysis and immunity measurements are conducted automatically.

2. Description of the Related Art

The apparatus for separate injection of reagents employed for the aforesaid installation wherein an automatic analysis is conducted is usually and generally of the type wherein, a separate injection nozzle is used to suck a necessary reagent thereinto from a reagent reservoir and the nozzle moves into alignment with a reaction vessel and discharges the sucked reagent into said reaction vessel.

FIG. 4 shows one example of such a prior-art apparatus for separate injection of reagents as stated above.

In the apparatus of this example, a separate injection nozzle 38 is retained in the turning fore end of a retainer 39 which is provided in such a manner that it is supported by a shaft 40 which can turn about its longitudinal axis and move vertically, and the upper end of this separate injection nozzle is connected to a reagent pump 41 through a flexible tube 54 so that a positive or negative pressure can be supplied into the nozzle. Numeral 42 denotes a motor which drives this reagent pump 41.

At prescribed positions inside the turning track of the aforesaid separate injection nozzle 38, a moving table 43 provided with a plurality of reagent reservoirs 45 and a moving table 50 having a number of reaction vessels 46 put on the upper side are disposed, and the moving table 43 is so designed that, rotated by a motor 44, it transfers a prescribed reagent reservoir 45 to the reagent suction position of the separate injection nozzle 38 to enable the suction of a reagent. The reaction vessels 46 are moved in and out of the position of where separate injection or discharge of the reagent takes place sequentially with the rotation of the moving table 50 by a motor 51. Besides, a reservoir 53 of a washing liquid 48 is connected through a selector valve 52 to the aforesaid flexible tube 54 connected to the reagent separate injection nozzle 38, so that the reagent remaining inside the separate injection nozzle after the discharge thereof can be washed away. This arrangement is made because there is the apprehension that another reagent selected in a subsequent separate injection operation by suction and discharge thereof is polluted, and so the separate injection nozzle 38 is moved to the position of a washing liquid port 47, where the washing liquid 48 is passed through said separate injection nozzle to wash the same.

However, the prior-art apparatus for separate injection of reagents constructed as described above has several problems.

For instance, although the washing liquid is passed through the separate injection nozzle to wash the inside thereof in order to prevent the mutual pollution of reagents as described above, it is not easy to wash the inside of the nozzle completely and a burden on the washing of the inside of the nozzle is not small in the field of the biochemical analysis wherein detection and measurement of a minute quantity of constituent are required. Even when washing with the required degree of core can be conducted, a considerably long time is needed for this washing and this hinders executing quick analytical operations.

In terms of a mechanism, the apparatus shown in FIG. 4 has a number of operating components and this produces a problem in that the apparatus is large in size and complicated.

In the practical separate injection of reagents, moreover, it is needed in some cases to inject a plurality of different kinds of reagents separately in one reaction vessel, and two methods can be thought of for the separate injection of these reagents in a plurality. The above-described apparatus for separate injection having the prior-art construction has a problem that it is not suited for either of these methods. According to one of these methods, a reagent reservoir 43 is rotated appropriately, reagents are sucked by the separate injection nozzle 38 from a plurality of reagent reservoirs 45 sequentially in such a manner that a first reagent is sucked first, a second reagent secondly and a third reagent further, and these reagents are discharged together into the reaction vessel 46 by separate injection. In this method, the time for rotating the moving table 43 and selecting each reagent and the time for sucking the reagent come by turns. Consequently, a quick analysis is hindered and, in addition, there occurs a problem of the apprehension of the mutual pollution of reagents since the nozzle is put in the reagents sequentially without being washed.

According to the other method, the operation of suction from the reagent reservoir and discharge into the reaction vessel 46 is repeated for every reagent and thereby the separate injection of a plurality of reagents is carried out. This method has a problem in that an extremely long time is required for the separate injection.

No problem of the mutual pollution of the reagents would take place and the separate injection of a plurality of reagents could be executed rapidly, of course, if the apparatus for separate injection were provided discretely for each reagent for conducting parallel separate injections. This method, however, would require an apparatus of an extremely complicated and large-sized construction, and therefore it is naturally unpractical and has no reality.

SUMMARY OF THE INVENTION

The present invention has an object to provide an apparatus for separate injection which solves these problems, has a simple and convenient construction, is free from the possibility of the mutual pollution of reagents and enables rapid separate injection of the reagents.

The characteristic features of the apparatus for separate injection of reagents of the present invention which realizes the above-stated object lie in that it is an apparatus for separate injection of reagents which injects one or a plurality of different kinds of reagents separately into open top type vessels set at positions of separate injection of reagents and which has a construction equipped with reagent reservoirs in the number of N (N is an integer of 2 or above) for storing different kinds of reagents respectively and arranged in a predetermined mutual positional relation, separate injection ports in the number of M (M is an integer of 1 to N) disposed fixedly at the positions of separate injection of reagents and being opposite to the top openings of the aforesaid vessels, liquid distribution tubes connecting these separate injection ports to an arbitrary reagent reservoir, dispensers provided separately for each of the reagent reservoirs so as to deliver a reagent liquid in each reagent reservoir to the separate injection port through the aforesaid liquid distribution tube, and drive means in the number of 1 to N for driving these dispensers for the reagent vessels selectively.

As for the aforesaid dispenser, a pump delivering the reagent liquid into the liquid distribution tube by a reciprocating operation of a plunger can be used but it is not limited thereto.

Besides, the drive means of the dispensers can be used commonly by disposing the plungers of the pumps for the dispensers in a plurality of positions on the same circumference of a circle and by providing only one operating lever for driving the pumps, which lever is rotatable around the center of this circle so that these pumps can be selectively driven.

The apparatus for separate injection of reagents of the present invention operates in the following way.

When a reaction vessel for a biochemical analysis is transferred to and stopped at the position for separate injection of reagents whereat the above-mentioned plurality of separate injection ports are provided, first an operating lever for driving the dispenser of the reagent reservoir to discharge the reagent into the reaction vessel is turned to select a necessary reagent out of a plurality of reagent reservoirs disposed on a concentric circle, and it is stopped just above the reservoir of the selected reagent. Then, said operating lever is moved downward by a vertical-motion mechanism to push the plunger of the dispenser, so as to pass a reagent liquid in the reagent through the distribution tube and inject it separately into the reaction vessel from the separate injection port. After the operation of separate injection, the aforesaid operating lever is moved upward and returns to the initial position.

In the case when the separate injection of another reagent is performed successively, the turning and downward motion of the aforesaid operating lever are conducted successively. In other words, first the separate injection of the first reagent is performed by the turning and vertical drive of the operating lever as described above, and in succession the separate injection of the second reagent is executed immediately by the next turning and vertical motion. Furthermore, separate injections of other reagents are executed successively as occasion demands. Accordingly, successive separate injections of a plurality of reagents can be executed only by the turning and vertical motion of the operating lever. In addition, no mutual pollution of the reagents occurs inside the distribution tube, since the distribution tube for each reagent is provided separately from others.

The above and other objects, features and advantages of the present invention will become more apparent from the following description of the preferred embodiment thereof taken in conjunction with the accompanying drawings, in which the same reference numerals denote the same elements.

DESCRIPTION OF THE PREFERRED EMBODIMENTS

Figure 1:
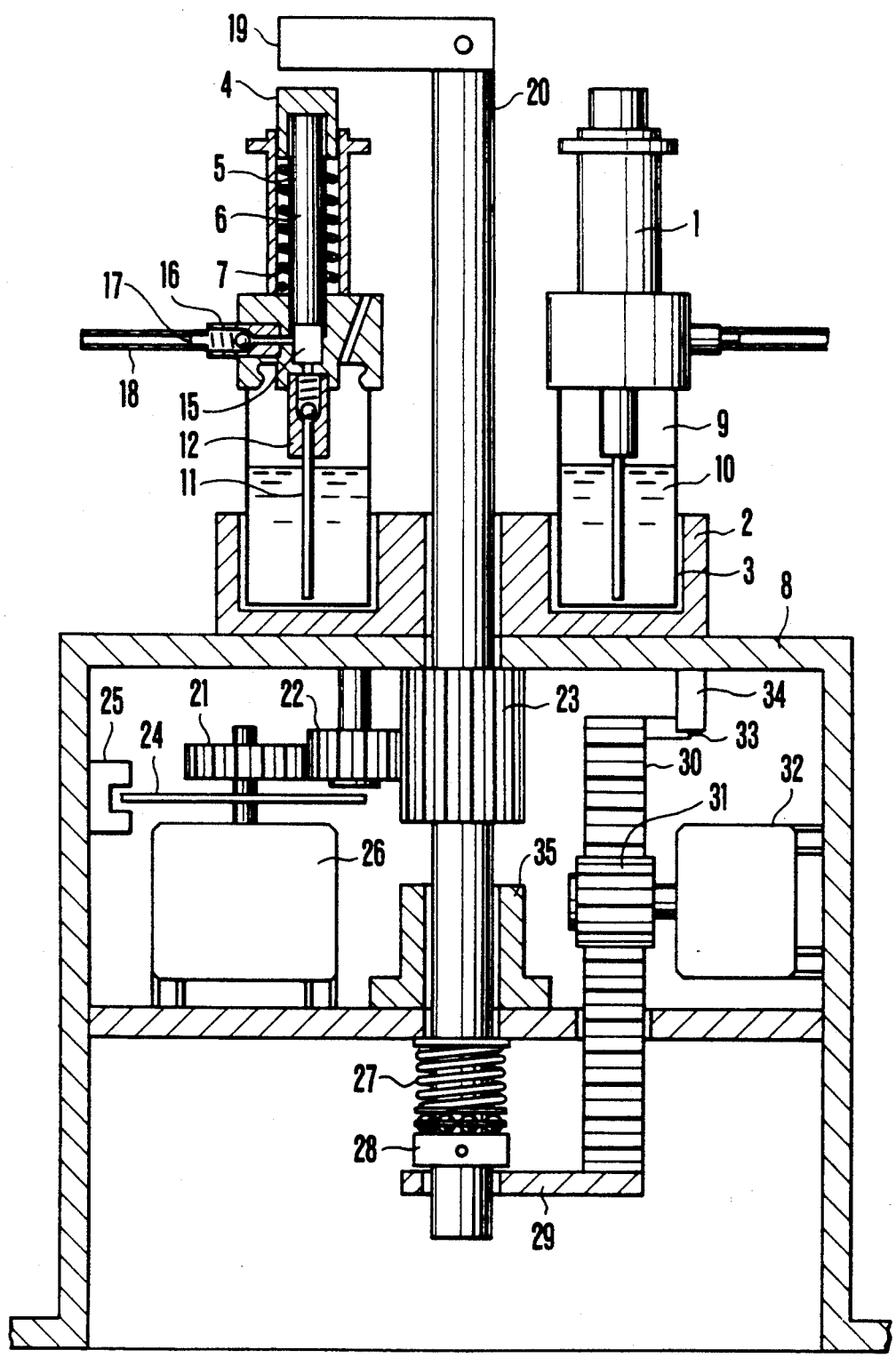
FIG. 1 is a schematic illustration of one example of a construction of an apparatus for separate injection of reagents according to the present invention.

The present invention will be described hereunder on the basis of an embodiment shown in the drawings.

Figure 2:
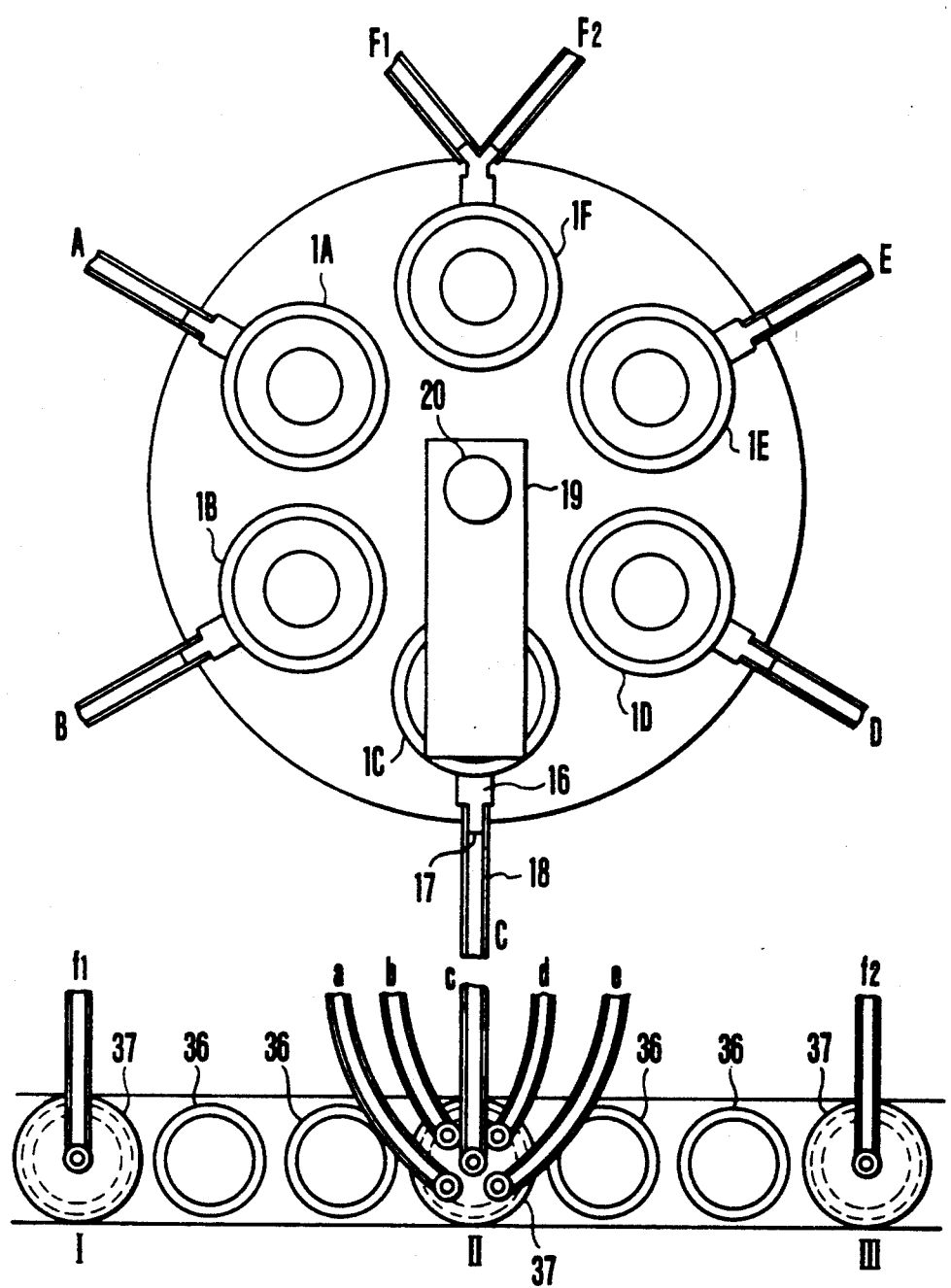
FIG. 2 is a schematic plan view of the apparatus of FIG. 1.
Figure 3:
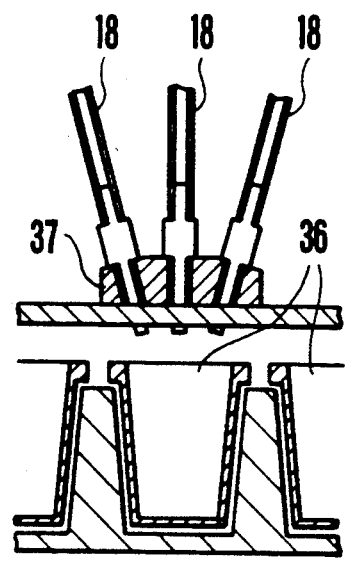
FIG. 3 is a partial sectional view showing the relationship between a reaction vessel and a separate injection port.
Figure 4:
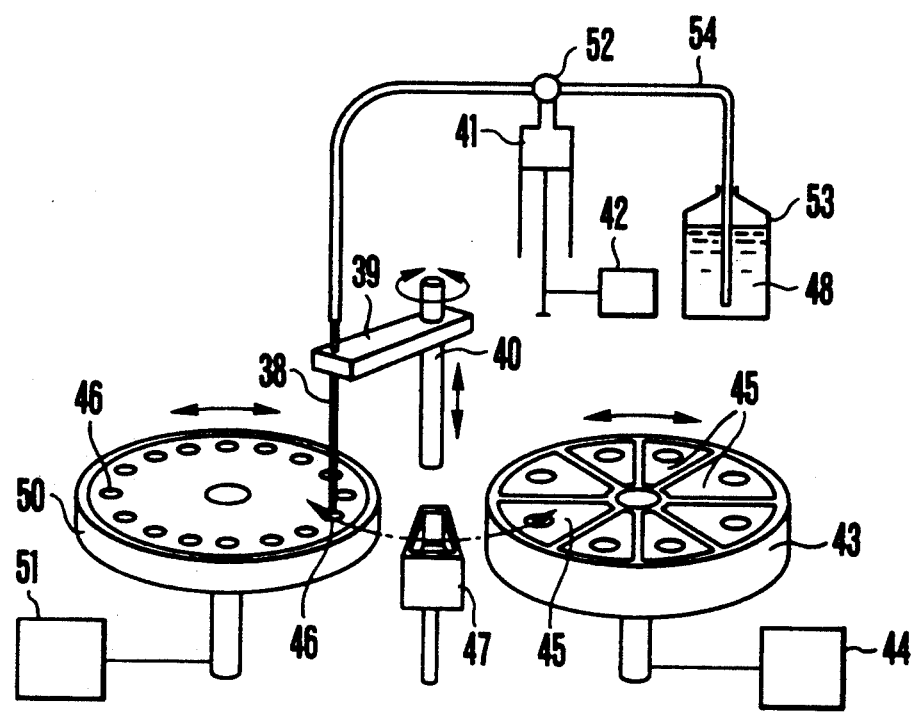
FIG. 4 is a schematic view of a prior-art apparatus for separate injection of reagents.

FIGS. 1 to 3 illustrate one example of the apparatus for separate injection of reagents according to the present invention. In these figures, numeral 9 denotes a reagent reservoir which is a cylindrical reservoir storing a reagent liquid 10 inside. A dispenser 1 is fitted on the top of the reservoir and said reagent liquid 10 is delivered from a discharge port 17 into a distribution tube 18 by the downward motion of a plunger 6. In more detail, this dispenser 1 is so designed that the plunger 6 held by a cylinder 5 is normally, biased upward by a spring 7 and upon movement an operating element 4 in the top part thereof which is pushed down by an operating lever 19 as will be described later, the reagent liquid held in a liquid reservoir 15 provided in the lower part of the cylinder 5 is delivered into the distribution tube 18 from a discharge valve 16 of a check valve type through the discharge port 17 mentioned above. On the occasion when the operating element 4 is moved upward for return by the force of the spring after it is pushed down, the liquid is pumped up into the aforesaid liquid reservoir 15 through the intermediary of a tube 11 dipped in the reagent liquid in the reagent reservoir and of a suction valve 12 of a check valve type. Accordingly, the aforesaid discharge valve 16 and suction valve 12 constitute a pump which delivers the reagent liquid from the reagent reservoir into the distribution tube in coordination with the reciprocating motion of the plunger 6.

In the construction of the apparatus, the above-mentioned dispenser 1 (hereinafter called a push-type dispenser) is mounted in the upper part, and a plurality of reagent reservoirs 9 holding different reagents respectively are disposed in the form that they are fitted in fitting holes 3 of a retaining table 2 which are formed at prescribed intervals on the circumference of a concentric circle as shown in FIGS. 1 and 2, while the aforesaid operating lever 19 is extended horizontally from and supported by the top part of a support 20 erected at the central position of said circumference and is turned and moved vertically by this support.

The aforesaid support 20 extend through the base plate of an apparatus stage 8 downward and is given rotation by a pulse motor 26 through a train of gears 21, 22 and 23. 24 denotes a slit disk and 25 a photosensor. By inputting a signal of this sensor to a control circuit not shown in the figures, said control circuit detects the rotational position of the pulse motor 26, and thereby the turning position of the operating lever 19 in the top part of the aforesaid support can be checked.

Besides, the aforesaid support 20 is splineconnected, for instance, to the aforesaid gear 23 so that it can move in the axial direction (the vertical direction in FIG. 1), and a compression spring 27 is provided between a flange 28 (a spring seat) on the lower end part thereof and a fixed part of the stage 8, so as to provide a biasing force to support 20 in the downward direction in FIG. 1. The downward force of the spring 27 on the support 20 is opposed by a stopper 29, and thereby the operating lever 19 is maintained in the state of FIG. 1. The aforesaid stopper 29 is moved down by driving a pinion 31 and a rack 30 by the rotation of a pulse motor 32, and the support is moved downward by the force of the spring 27. Numeral 33 denotes a flag fixed to the rack 30, and 34 a photosensor fixed to the stage 8, whereby the home position in the vertical direction of the support is set.

The quantity of the reagent to be delivered is determined by a distance of the downward motion of this support 20, and in the case when it is needed to change a necessary quantity of reagent to be delivered, according to an object of measurement, a distance of movement of the rack 30 from the home position can be given by setting the number of rotations of the pulse motor 32 variably by a control circuit not shown in the figures. Numeral 35 denotes a support guide fixed to the fixed part of the stage 8.

According to the construction described above, the operating lever 19 is positioned oppositely above one of the plurality of reagent reservoirs disposed on the circumference of a concentric circle by turning the support 20, and by moving this support downward subsequently, the reagent liquid in the liquid reservoir 15 of the dispenser 1 can be delivered into the distribution tube 18. The reagent liquid is supplemented to the liquid reservoir 15 from the reagent reservoir 9 by the upward motion of return of the operating lever. The end parts of distribution tubes 18 connected to reagent vessels 1A to 1E are denoted by A to E respectively, while a distribution tube F corresponding to a reagent vessel 1F has branches $F_1$ and $F_2$. The other ends of the distribution tubes 18 are designated by a to e respectively and the other ends of the distribution tubes $F_1$ and $f_2$ are designated $f_1$ and $f_2$ respectively.

The ends a to e of the distribution tubes are fixed to a common distribution head 37 at the position II separate injection as shown in FIG. 2, and the end $f_1$ of one branch of the distribution tube F is fixed to the head 37 at the position I of separate injection, while the end $f_2$ of the other branch of the distribution tube F is fixed to the head 37 at the position III of separate injection. By driving the dispenser 1 of each reagent reservoir, according to this constitution, an aimed reagent liquid can be injected separately into a prescribed reaction vessel 36 at a prescribed position of separate injection. In addition, an advantage is produced on the occasion that there is no possibility of a distribution channel of each reagent liquid causing the mutual pollution with any other, since each distribution tube 18 is separate completely from others.

As to the reagent in the reagent reservoir 1F, it can be injected separately in different reaction vessels at the same time at the positions I and III of separate injection.

The present invention is not limited, of course, to the mode of the embodiment described above, but can be embodied in various modified modes. For instance, a construction wherein a temperature-regulating device is provided as an attachment to the reagent reservoir can be adopted.

The apparatus for separate injection of reagents according to the present invention provides that a plurality of reagents can be injected separately with complete removal of mutual pollution thereof by a small-sized and simple mechanism, and that successive separate injection can be performed in a very short time, and it can be used very suitably, in particular, for a biochemical analysis installation and an immunity measuring installation wherein the mutual pollution of reagents causes false measurement directly.

Besides, the apparatus for separate injection of reagents of the present invention can meet effectively the demand for quick execution of the separate injection of a plurality of reagents by a small-sized apparatus, since it uses a system wherein a plurality of dispensers are driven selectively by using the common driving mechanism.

What is claimed is:

1. An apparatus for selectively injecting a reagent into a reaction chamber comprising:
   a plurality of reagent reservoirs, each adapted to contain a different reagent, support means for supporting said reagent reservoirs in a circular configuration, separate dispenser means mounted on top of each reservoir, each dispenser means including a liquid holding chamber, inlet means connected to said chamber and adapted to extend downwardly into a reagent in said reagent reservoir, outlet means connected to said chamber and spring biased plunger means extending into said chamber, dispenser actuating means adapted to be selectively aligned with said plunger means of each dispenser means for selectively depressing and releasing said spring biased plunger means and distribution means connected to said outlet means of each dispenser means for distributing each reagent separately to a reaction chamber,
   wherein said dispenser actuating means includes a vertically moveable support rod disposed centrally of said support means for supporting said reagent reservoirs and having horizontally extending lever means adapted to selectively engage said plunger means and drive means for rotating said support rod to selectivley position said lever means above a plunger means and for vertically moving said lever means into and out of engagement with said plunger means.

2. An apparatus as set forth in claim 1, wherein said distribution means is connected to an outlet means of each dispenser means for individually distributing each reagent to a selected on or ones of a plurality of separate reaction chambers.

3. An apparatus as set forth in claim 2, wherein said means for individually distributing each reagent comprises a plurality of distribution tubes each connected at one end to respective outlet means and distribution head means connected to an opposite end of each distribution tube for directing respective reagents into a selected reaction chamber or chambers.

4. An apparatus as set forth in claim 3, wherein a plurality of said distribution tubes are connected to a common distribution head means.

* * * * *